(12) United States Patent
McCurdy et al.

(10) Patent No.: US 12,144,953 B2
(45) Date of Patent: Nov. 19, 2024

(54) ELECTRONIC MULTI-LAMP PEN FOR ACTIVATING PHOTO-RESPONSIVE MATERIALS

(71) Applicants: HYPRSKN INC., New York, NY (US); THE REGENTS OF THE UNIVERSITY OF COLORADO, Denver, CO (US)

(72) Inventors: Keith McCurdy, New York, NY (US); Carson Bruns, Boulder, CO (US); Jesse Butterfield, Boulder, CO (US); Jon Osis, New York, NY (US)

(73) Assignees: HYPRSKN INC., New York, NY (US); THE REGENTS OF THE UNIVERSITY OF COLORADO, Denver, CO (US)

( * ) Notice: Subject to any disclaimer, the term of this patent is extended or adjusted under 35 U.S.C. 154(b) by 0 days.

(21) Appl. No.: 18/405,270

(22) Filed: Jan. 5, 2024

(65) Prior Publication Data

US 2024/0226522 A1     Jul. 11, 2024

Related U.S. Application Data

(60) Provisional application No. 63/478,583, filed on Jan. 5, 2023.

(51) Int. Cl.
| | | |
|---|---|---|
| *A63H 33/22* | (2006.01) | |
| *A61M 37/00* | (2006.01) | |
| *G02F 1/01* | (2006.01) | |
| *G02B 5/23* | (2006.01) | |

(52) U.S. Cl.
CPC ....... *A61M 37/0076* (2013.01); *G02F 1/0126* (2013.01); *A61M 2205/053* (2013.01); *A61M 2205/50* (2013.01); *A61M 2210/04* (2013.01); *G02B 5/23* (2013.01)

(58) Field of Classification Search
CPC ........ A61M 37/0076; A61M 2205/053; A61M 2205/50; A61M 2210/04; G02F 1/0126; G02B 5/23
See application file for complete search history.

(56) References Cited

U.S. PATENT DOCUMENTS

| | | | | |
|---|---|---|---|---|
| 5,272,234 | A * | 12/1993 | Chen ................... | G02B 5/23 526/287 |
| 7,249,431 | B1 * | 7/2007 | Rose .................. | G09F 13/20 250/483.1 |
| 2007/0048065 | A1 * | 3/2007 | Schmidt ............. | B43L 1/02 401/109 |

* cited by examiner

*Primary Examiner* — Elmito Breval
(74) *Attorney, Agent, or Firm* — Geoffrey Lottenberg; Berger Singerman LLP

(57) ABSTRACT

A device for photoexcitation of a photo-responsive material, such as a photochromic material, includes a pen-type housing having a UV lamp at one end and a visible light lamp at the other end. The device includes a microcontroller, a power supply, and an input device such as button, microphone, temperature sensor, or accelerometer. The beam width of the lamps can be adjusted by a lens adjacent to the respective lamps. The device is designed to photoexcite the photo-responsive material into various states depending on the type and wavelength of light emitted from the device. The device enables writing and erasing on a substrate, such as human skin, that contains or is embedded with the photo-responsive material, by exposing the material to light emitted from the device.

20 Claims, 5 Drawing Sheets

ELECTRONIC MULTI-LAMP PEN FOR ACTIVATING PHOTO-RESPONSIVE MATERIALS

CROSS REFERENCE TO RELATED APPLICATIONS

This application claims priority to and the benefit of U.S. Provisional Application Ser. No. 63/478,583 filed on Jan. 5, 2023.

FIELD OF INVENTION

This invention relates to the design and methods of use for a rechargeable electronic handheld device designed to write and erase information in a substrate, such as human tissue or skin, that is applied with or contains appropriate photochromic dyes or pigments, or other photo-responsive materials such as fluorescent and phosphorescent compounds. The components of the device are contained in a housing resembling a writing pen. In an embodiment, a tip is designed for writing information with an ultraviolet lamp comprising one or more ultraviolet light emitting diodes (LEDs) and the opposing end is designed to erase and/or write information with an ultraviolet and/or visible lamp comprising one or more ultraviolet and/or visible light LEDs. The device is designed to be used safely with photochromic and other photo-responsive materials applied to a target substrate, including the human skin.

BACKGROUND OF THE INVENTION

Photo-responsive materials, such as photochromic dyes and pigments, which express visible color changes upon exposure to certain frequencies of light (photoexcitation), can be applied to, or incorporated in, physical materials in order to confer them with photochromic properties. Examples of commercially available photochromic materials include sunlight-reactive garments, paper sheets, plastic films, and even personal ultraviolet sensors such as colorimetric radiometers and dosimeters. An emerging use case for photochromic materials involves their use as re-writable dyes or pigments for creative expression through human skin. The present invention is an electronic multi-lamp device in the form factor of a writing utensil that unlocks the ability to write and erase, or shift the color of, images that can be written in or on skin containing photochromic (or other photo-responsive) material, or otherwise carry out these actions on other substrates containing photochromic material that are photoexcitable by ultraviolet and visible light.

SUMMARY OF THE INVENTION

The present invention contemplates various embodiments for a handheld rechargeable electronic lamp containing a plurality of light emitting diodes of different wavelengths, contained in a housing resembling a writing pen, which can be used to write and erase images or text in photo-responsive materials, including photochromic materials, through photoexcitation. In some embodiments, at the tip or distal end of the pen is an adjustable-beam ultraviolet (UV) lamp, and at the opposite or proximal end of the pen is a visible light lamp capable of producing red, green, blue, and white light (RGBW) or any combination of visible light derived thereof.

In some embodiments, the opposite or proximal end may include an ultraviolet light source in addition to, or in lieu of, the visible light source.

In some embodiments, the pen includes one or more indicator lights, one or more input devices including buttons, an accelerometer, a temperature sensor, and a microphone for controlling the lamps, adjustable lenses for controlling the beam dimensions, a microcontroller, a lithium-ion battery, and a connection port for data transfer and battery charging purposes.

The present invention also provides methods of using the device including writing, erasing, and/or changing the appearance of any substrate containing or comprising photochromic materials or other photo-responsive (fluorescent, phosphorescent, etc.) materials. In some embodiments, the photochromic-containing substrate comprises biocompatible UV-activated bistable or multi-stable P-type photochromic dyes or pigments. These photochromic materials can be applied onto or into the dermal or epidermal layers of human skin. The photochromic pigments may be adhered to the skin's surface or implanted in dermal or epidermal layers of skin using techniques such as those used to create tattoos, permanent makeup, or temporary tattoos. These photochromic skin markings rely on biocompatible photochromic dye or pigment particles to imbue skin with the ability to change color when exposed to specific wavelengths of light. The photochromic approach to writing, erasing, and re-writing information in the skin enables the ability to quickly change body art at will without pain as often and as many times as one desires.

BRIEF DESCRIPTION OF THE DRAWINGS

Reference should be made to the following detailed description, taken in connection with the accompanying drawings, in which.

DETAILED DESCRIPTION

Figure 1:
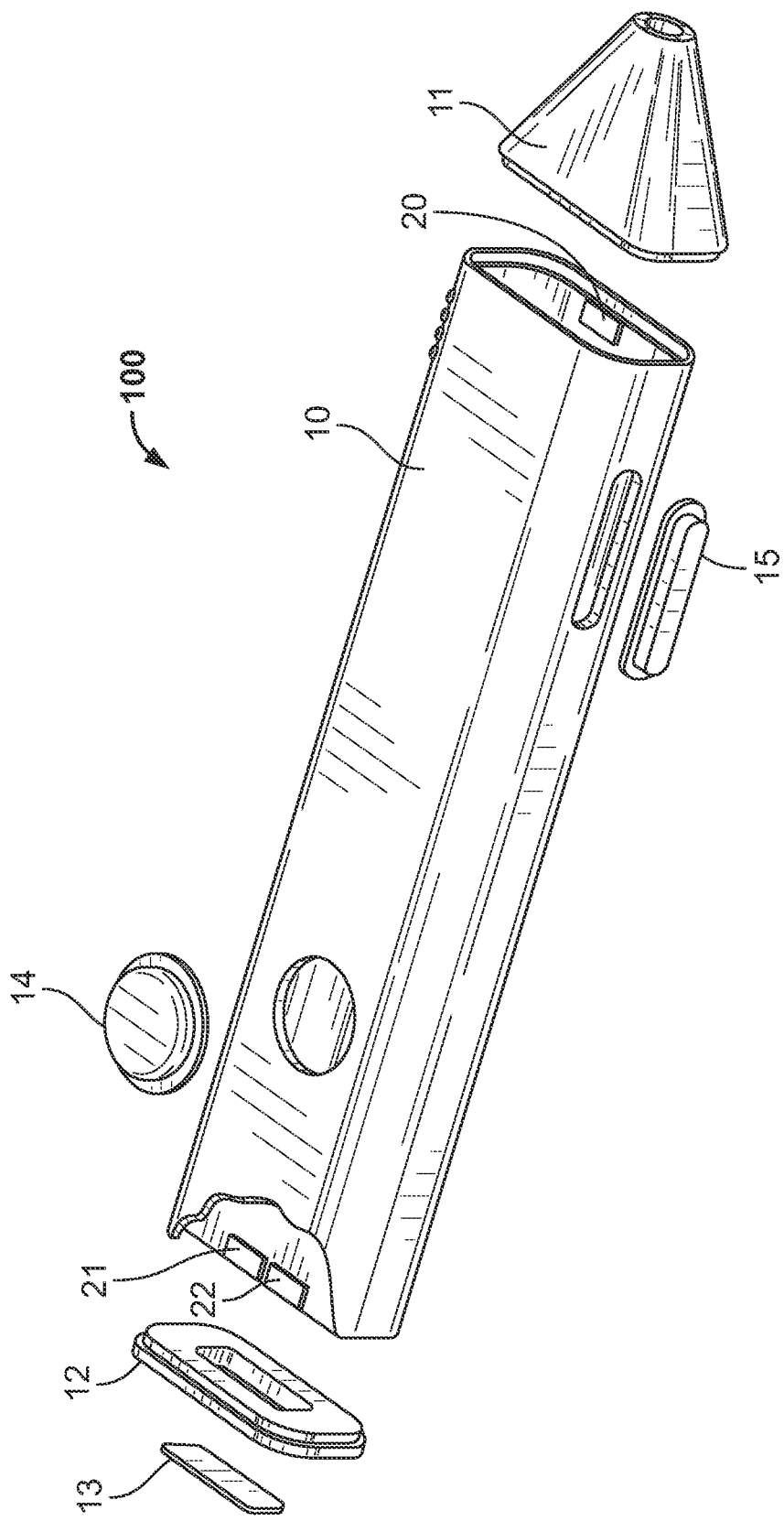
FIG. 1 is an exploded view of an example of the electronic multi-lamp pen.

In the following description, for the purposes of explanation, numerous specific details are set forth to provide a thorough understanding of the invention. It will be apparent, however, to one skilled in the art that the invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations of thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "some embodiments," "one embodiment" or "an embodiment" means that a particular feature, structure, or characteristic described in connection with the embodiment is included in at least one embodiment of the present invention. Thus, appearances of the phrases "in some embodiments," "in one embodiment" or "in an embodiment" in various places throughout this specification are not necessarily all referring to the same embodiment. Furthermore, the particular features, structures or characteristics may be combined in any suitable manner in one or more embodiments.

Temporary and permanent tattoos and permanent makeup are made by applying dyes or pigments to skin. Deeper layers of skin (dermis) and highly stable pigments, at least hundreds of nanometers in diameter, create the most permanent tattoos, whereas dyes or pigments applied superficially to the skin's surface create the most temporary tattoos. Temporary and permanent tattoos and permanent makeup typically rely on conventional dye and pigment colorants. However, photochromic dyes and pigments and other photo-responsive materials such as fluorescent or phosphorescent materials can also be suitable for use on or in human skin, and other substrates. Although most tattoo and permanent makeup pigments are stable colorants that do not readily undergo color-changing reactions in the dermis, photochromic tattoos and permanent makeup can undergo a photochemical reaction that generates a color change when activated by light of an appropriate wavelength. In T-type photochromic dyes, this photochemical reaction is thermally reversible, so the dye returns to its original state spontaneously when the activating light is removed. P-type photochromic dyes are not thermally reversible, and therefore do not spontaneously return to their original color after activation. Instead, reversal of photochemical activation in P-type dyes is accomplished by a second photochemical activation of a different wavelength range. Therefore, information can be written photographically and stored long-term in P-Type photochromic materials under appropriate lighting conditions.

The present invention contemplates a handheld electronic device designed to photo-responsively write and erase information on or within a target substrate, including human skin containing or applied with photochromic or photo-responsive materials as well as other photochromic and photo-responsive materials beyond skin, such liquids, gels, powders, films, paper, glass, plastics, and the like. Embodiments of the invention comprise a device comprising electronic components in the form of a handheld housing resembling a pen used for writing, which pen contains both UV and visible light lamps. Embodiments of the present invention also contemplate systems and methods of utilizing this device for writing, erasing, or changing the visible features of photochromic and photo-responsive materials.

With reference to FIGS. 1-4, in some embodiments, provided is a handheld, rechargeable electronic device 100 containing a plurality of lamps. In some embodiments, the device is configured such that it is capable of exposing photo-responsive materials to ultraviolet light from one end and colored or white visible light from the opposite end. In some embodiments, the opposite end includes an ultraviolet light in lieu of or in addition to the visible light. In some embodiments, the device is optimized for use with P-type photochromic materials applied to a target substrate such as the human skin or other material.

Housing. In some embodiments, the housing 10 of the device 100 comprises precision-machined material, such as plastic, aluminum, or stainless steel. In some embodiments, housing 10 includes a plurality of LEDs, a microcontroller, a power supply such as a lithium-ion battery, one or more lenses, and a connection port. As one example, as shown in the Figures, the housing 10 has a rectangular or trapezoidal cuboid shape. In other examples, the housing 10 has a cylindrical shape.

Figure 2:
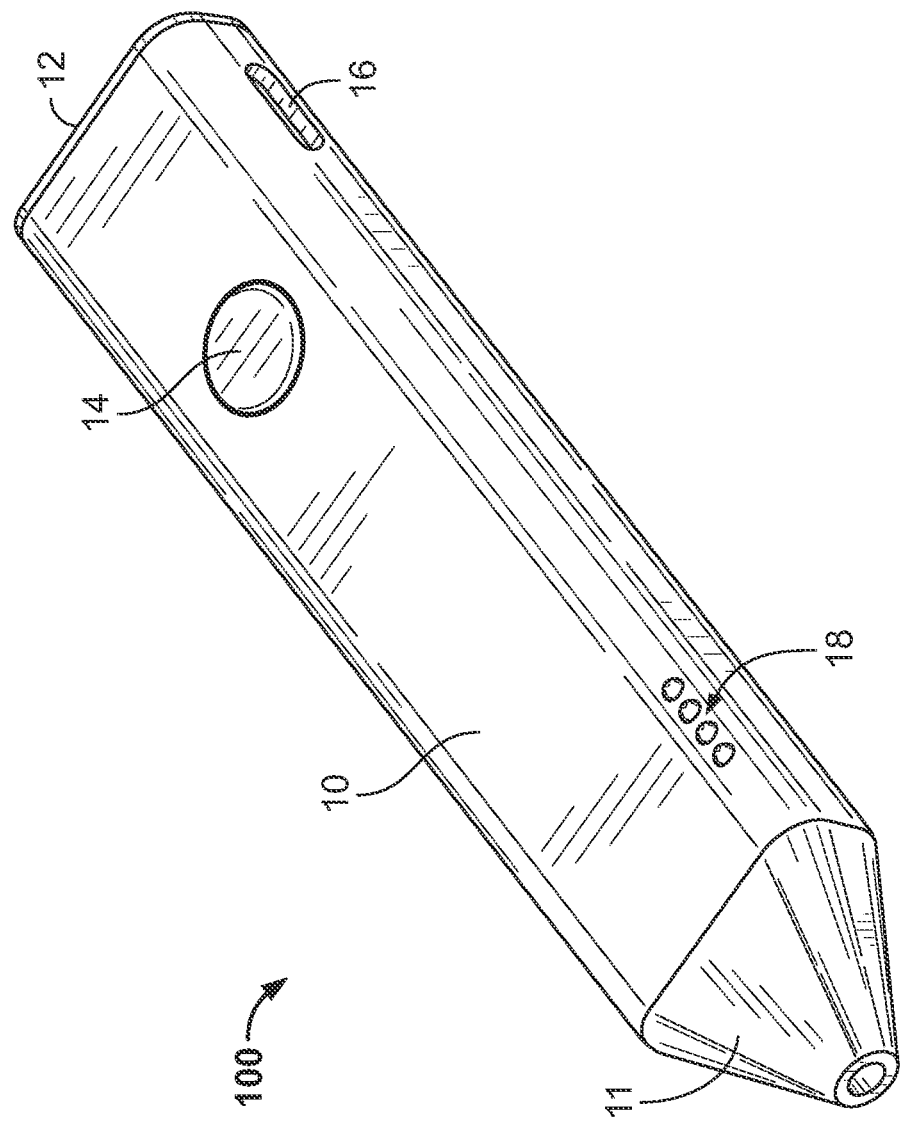
FIG. 2 is a perspective view of an example of the electronic multi-lamp pen.

In some embodiments, the front or distal end of the device 100 comprises a tip 11 with a lens 17. The tip 11 may be permanently affixed to the housing 10 or removably affixed thereto by a threaded connector, snap-fit, or interference fit. The rear or proximal end of the device 100 includes cap 12 with lens 13. The cap 12 may be permanently affixed to the housing 10 or removably affixed thereto by a threaded connector, snap-fit, or interference fit. In some embodiments the device 100 includes one or more physical input devices including a top button 14 and a side button 15. With reference to FIG. 2, the housing 10 of the pen 100 includes in some embodiments a connection port 16 which may, for example, comprise a USB-C port.

Figure 3C:
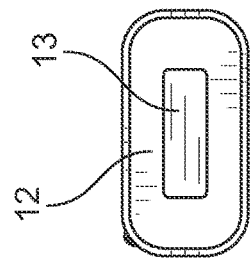
FIG. 3C is a rear view of an example of the electronic multi-lamp pen.
Figure 3B:
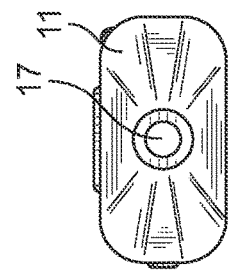
FIG. 3B is a front view of an example of the electronic multi-lamp pen.
Figure 3D:
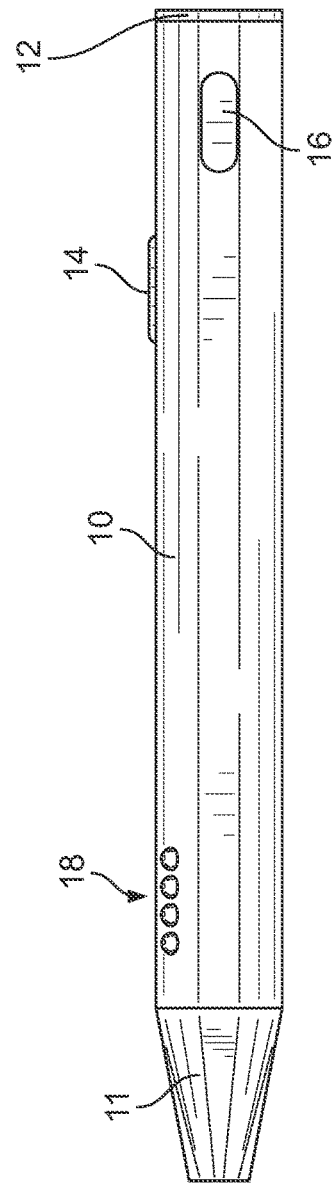
FIG. 3D is a side view of an example of the electronic multi-lamp pen.
Figure 3A:
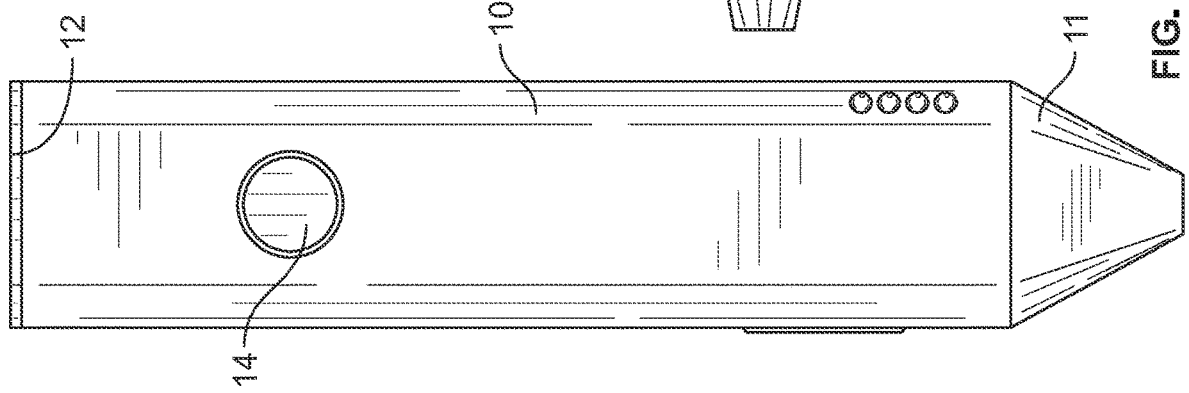
FIG. 3A is a top view of an example of the electronic multi-lamp pen.

In some embodiments, the front of the housing 10, about the tip 11, includes a UV lamp 20 which emits light toward the tip 11 and through and out of lens 17 (see FIG. 3B). In some embodiments, the UV lamp 20 comprises one or more UV LEDs In some embodiments, the housing 10, for example at the tip 11, includes a cam mechanism that causes the distance between the UV LED and the lens 17 to change when the cam is rotated, causing a change in dimensions of the ultraviolet beam when powered on. In some embodiments, the rear of the housing 10, about the cap 12, includes one or more lamps 21 and 22 which emit light through the lens 13. In some embodiments, the lamps 21 and 22 comprise UV LEDs, visible light LEDs, or combinations thereof.

Figure 4:
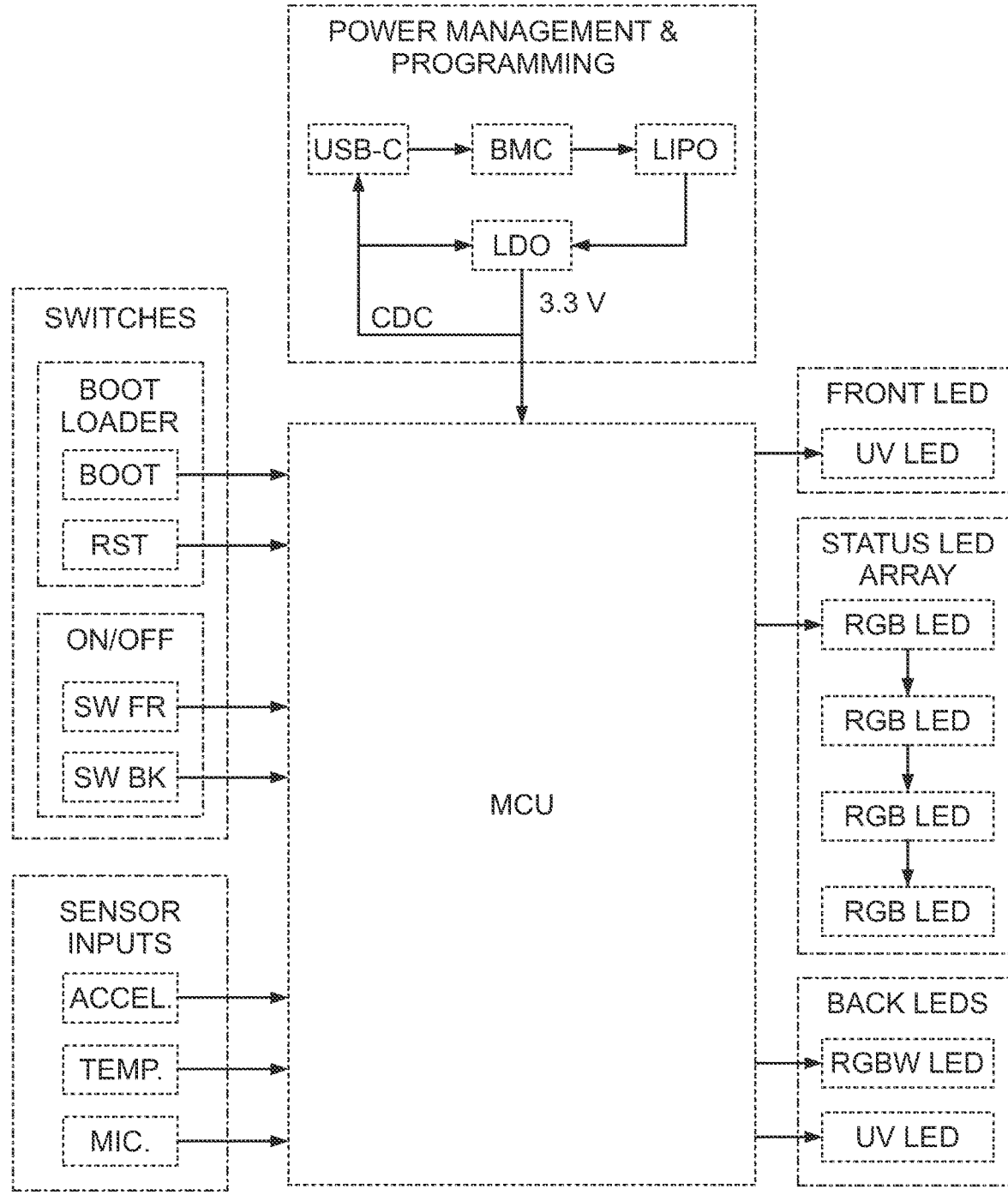
FIG. 4 is a schematic of the electronic components of the electronic multi-lamp pen.

Microcontroller. In some embodiments, the internal components held within the housing 10 are arranged around a printed circuit board equipped with a microcontroller, other components discussed below, and support components such as transformers and capacitors to ensure safe operation of the device. FIG. 4 is an exemplary schematic showing the components thereof including a microcontroller or MCU. In preferred embodiments, the microcontroller interfaces with the front UV lamp 20 and the back lamps 21 and 22 and, in some embodiments, is used to control the luminous intensity of the lamps by pulse-width modulation. In some embodiments, the microcontroller is also used to process data recorded from input devices including buttons 14 and 15, an accelerometer, a temperature sensor, and/or a microphone which are used to render commands that control the status of the device, such as on/off, dim/bright, ultraviolet/visible, and the like.

Power Supply. In some embodiments, the MCU and related components are powered by power supply comprising a battery to enable portability. In some embodiments, the housing includes a shape-complementary rechargeable lithium-ion battery in electrical communication with the printed circuit board, which supplies power to all subcomponents of the device that draw power.

Indicator lights. In some embodiments the MCU interfaces with an optional status LED array 18 comprising a plurality of visible light LEDs which are externally visible and can depict various states of the device including charge level, light intensity level, and the like. For example, the charge status of the battery is indicated by the color of one or more of the visible light LEDs that can be viewed through an aperture on the sidewall of the housing 10. In some embodiments, the indicator LEDs emit green light when the charge exceeds 66% of maximum capacity, orange light when the battery charge is between 33-66% of its maximum capacity, and red light at charge levels below 33% maximum capacity.

Lamps. In some embodiments, the lamp 20 employed at the front or distal end of the housing 10 is a 1000-mW ultraviolet LED with a peak wavelength of 365 nm contained in the housing 10. In some embodiments, one or both of the lamps 21 and 22 employed as the back or proximal end of the housing 10 is a bright RGB light emitting diode package capable of emitting white light exceeding at least 100 lumens. Optionally, one or both of the lamps 21 and 22 may comprise a UV LED of the same or similar specifications to that at the front.

Lenses. In some embodiments, the tip 11 and cap 12 contain internal glass lenses near their termini, enabling beam-width adjustment as described above. In some embodiments, the lenses may be coated with optical bandpass filters to exclude portions of the emitted light spectrum.

Buttons. In some embodiments, buttons 14 and 15 are mounted on the top of the upper housing and/or the sidewalls as a means of input for controlling the device settings with various click inputs. These input devices are in electronic communication with the MCU and, in some embodiments, button 14 is used to activate one or both of the front and back LEDs and the button 15 is used as an input device to access the bootloader and carry out various functions of the MCU.

Accelerometer. In some embodiments, the printed circuit board that controls the device also includes an accelerometer that reports position and motion data to the microcontroller. In these embodiments, the data reported by the accelerometer is used to encode device settings such as lamp activation and power input by the user.

Microphone. In some embodiments, the printed circuit board holds a microphone that reports auditory data to the microcontroller. In these embodiments, the data reported by the microphone is used to encode device settings, such as luminous intensity, input by the user.

Temperature Sensor. In some embodiments, the printed circuit board holds a temperature sensor. The sensor may monitor and report temperature readings to the user via an accompanying mobile app. The temperature sensor may also report readings to the microcontroller to trigger various functions.

The present invention also contemplates embodiments of a method of using the device described above, including its use in conjunction with a photochromic-containing substrate to enable writing, erasing and/or creative expression.

Figure 5:
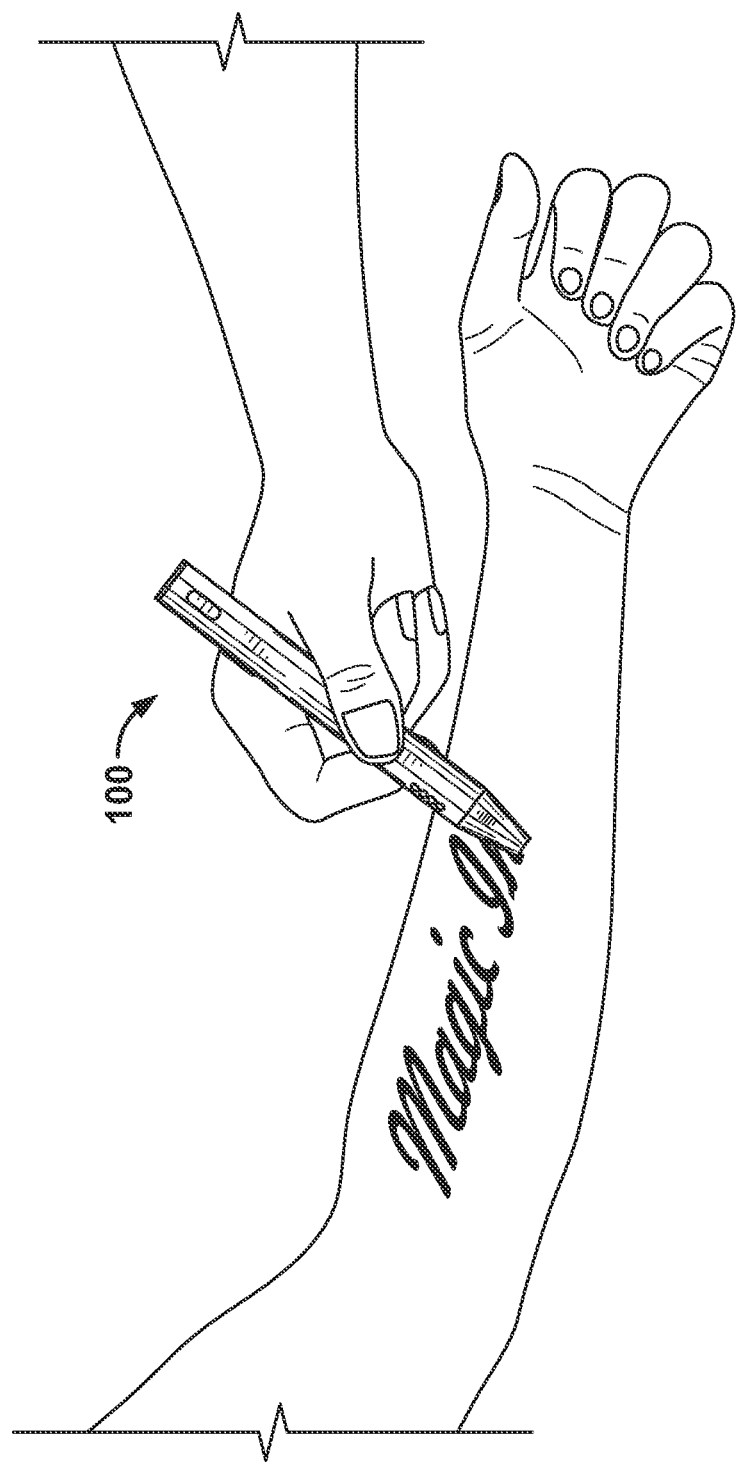
FIG. 5 is an image depicting the use of the electronic multi-lamp pen in some embodiments that allows it to write and erase images in pigments contained within or on human skin.

For example, the image in FIG. 5 indicates how a body art design can be reversibly and repeatably written, then erased, and then re-written with UV, visible, and UV light, respectively. This method allows the user to change their tattoo design using only the handheld multi-lamp as a writing utensil. In some embodiments, skin-safe photochromic material is applied onto or embedded into the human skin. In one example, the skin-safe photochromic material becomes more visibly colored upon exposure to ultraviolet light, whereas it becomes less visibly colored (erased) by exposure to appropriate wavelengths of visible light, depending on the specific photochromic formula. Therefore, the ultraviolet-light "tip" of the pen is used to write features, while the visible-light "eraser" of the pen is used to remove features, in a photochromic material.

It is appreciated and understood that although some embodiments of the device are designed specifically for use with skin-safe photochromic pigments for temporary and permanent body art or makeup, the same functions can also be applied to any substrate containing photochromic materials, including photochromic-containing liquid, gel, powder, film, paper, glass, plastic, and the like.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations, and variations will become apparent to those of ordinary skill in the art in light of the foregoing description. Accordingly, it is intended that the present invention embrace all such alternatives, modifications and variations as fall within the scope of the appended claims. The fact that a product, process, or method exhibits differences from one or more of the above-described exemplary embodiments does not mean that the product or process is outside the scope (literal scope and/or other legally recognized scope) of the following claims.

What is claimed is:

1. A device for photoexcitation of a photo-responsive material, comprising:
a housing including an ultraviolet lamp at one end and a visible light lamp at an opposing end;

wherein the ultraviolet lamp is configured to emit light at a wavelength sufficient to photoexcite the photo-responsive material into a first state; and wherein the visible light lamp is configured to emit light at a wavelength sufficient to photoexcite the photo-responsive material into a second state.

2. The device of claim 1, including a microcontroller enabling electronic control of each of the ultraviolet lamp and the visible light lamp.

3. The device of claim 2, including a power supply in electrical communication with the microcontroller.

4. The device of claim 3, wherein the power supply comprises a rechargeable battery.

5. The device of claim 3, wherein the microcontroller is in electrical communication with a connection port for data transfer and charging of the power supply.

6. The device of claim 2, including one or more input devices including a button, an accelerometer, a microphone, a temperature sensor or combinations thereof, the input devices each in electrical communication with the microcontroller for modifying the operational state of the device.

7. The device of claim 1, wherein the housing includes a tip at a distal end and a cap at a proximal end.

8. The device of claim 1, wherein at least one of the ultraviolet lamp and the visible light lamp is adjacent to an adjustable lens, the adjustable lens configured to modulate beam width of the lamp.

9. The device of claim 1, wherein the ultraviolet lamp comprises a 1000 mW UVA light emitting diode capable of emitting light at a peak wavelength of 365 nm.

10. The device of claim 1, wherein the visible light lamp comprises one or more light emitting diodes configured to emit red, green, and blue light and produce white light of up to at least 100 lumens.

11. The device of claim 1, wherein the photo-responsive material comprises a photochromic material.

12. A method for photoexcitation of a photochromic or photo-responsive material, comprising:
   a. providing a device comprising an ultraviolet lamp and a visible light lamp;
   b. providing a substrate containing the photochromic or photo-responsive material;
   c. activating the ultraviolet lamp to emit light at a wavelength sufficient to photoexcite the photochromic or photo-responsive material into a first state; and
   d. exposing the photochromic material to the light emitted from the ultraviolet lamp.

13. The method of claim 12, further including the steps of activating the visible light lamp to emit light at a wavelength sufficient to photoexcite the photochromic or photo-responsive material into a second state and exposing the photochromic material to the light emitted from the visible light lamp.

14. The method of claim 12, wherein the substrate comprises human skin.

15. The method of claim 12, wherein the substrate comprises liquid, gel, powder, film, paper, glass, plastic, and combinations thereof.

16. The method of claim 12, wherein the device includes a microcontroller enabling electronic control of each of the ultraviolet lamp and the visible light lamp.

17. The method of claim 16, including a power supply in electrical communication with the microcontroller and one or more input devices including a button, an accelerometer, a microphone, a temperature sensor or combinations thereof, the input devices each in electrical communication with the microcontroller for modifying the operational state of the device.

18. The method of claim 12, wherein at least one of the ultraviolet lamp and the visible light lamp is adjacent to an adjustable lens, the adjustable lens configured to modulate beam width of the lamp.

19. The method of claim 18, wherein the ultraviolet lamp comprises a 1000 mW UVA light emitting diode capable of emitting light at a peak wavelength of 365 nm.

20. The method of claim 18, wherein the visible light lamp comprises one or more light emitting diodes configured to emit red, green, and blue light and produce white light of up to at least 100 lumens.

* * * * *